United States Patent [19]

Sikkenga et al.

[11] 4,433,190
[45] Feb. 21, 1984

[54] PROCESS TO CONVERT LINEAR ALKANES

[75] Inventors: David L. Sikkenga, Wheaton; Thomas D. Nevitt, Naperville; Norman F. Jerome, Elmhurst, all of Ill.

[73] Assignee: Standard Oil Company (Indiana), Chicago, Ill.

[21] Appl. No.: 422,821

[22] Filed: Sep. 24, 1982

[51] Int. Cl.³ .................. C07C 5/124; C07C 5/30; C07C 5/36; C07C 5/40
[52] U.S. Cl. .................. 585/660; 585/525; 585/664; 585/670; 585/671; 502/202; 502/60; 502/77
[58] Field of Search .............. 585/312, 322, 329, 415, 585/417, 418, 419, 510, 520, 525, 531, 664, 666, 670, 671; 252/432

[56] References Cited

U.S. PATENT DOCUMENTS

4,268,420 5/1981 Klotz .................. 585/640

Primary Examiner—Delbert E. Gantz
Assistant Examiner—A. Pal
Attorney, Agent, or Firm—Wallace L. Oliver; William T. McClain; William H. Magidson

[57] ABSTRACT

A process to convert an alkane, such as n-butane, to dehydrogenated and isomerized products comprises contacting such alkane under conversion conditions with an AMS-1B crystalline borosilicate catalyst composition containing an ion or molecule of a catalytically active element, such as a noble metal.

28 Claims, 1 Drawing Figure

PROCESS TO CONVERT LINEAR ALKANES

BACKGROUND OF THE INVENTION

This invention relates to conversion of linear alkanes, such as n-butane and more particularly relates to conversion of n-butane to higher value hydrocarbons such as butylenes, isobutane and aromatics using an AMS-1B crystalline borosilicate-based catalyst.

In many instances it is desirable to convert an alkane such as linear alkane or a molecule containing a linear alkane segment into an alkene by dehydrogenation, a branched molecule by structural isomerization, or an aromatic species. Such alkenes and branched molecules then can be reacted further such as by polymerization or oxidation to form useful products. Normal butane is a linear alkane containing four carbon atoms which is obtained commercially by separation from natural gas and as a petroleum refinery by-product. As such, n-butane is a relatively inexpensive feedstock. However, isobutylene is a branched four-carbon olefin monomer useful in the manufacture of polyisobutylenes which can have various properties depending on the manner of polymerization. For example, both crystalline polyisobutylene and viscous polyisobutylene can be manufactured according to well-known processes in the art. In addition, isobutylene is used in the manufacture of methyl-t-butyl ether which is useful as an octane booster in gasoline. Conventionally, butylenes, including isobutylene, are obtained as a by-product from refinery processes such as catalytic or thermal cracking units. For manufacture and uses of butylenes, see Kirk-Othmer, "Encyclopedia of Chemical Technology," Third Edition, Vol. 4, pp. 346-375, incorporated herein by reference.

Aromatic species such as benzene, toluene and xylenes are well-known to have many commercial utilities as chemical feedstocks and in gasoline-grade liquids.

Zeolitic materials, both natural and synthetic, are known to have catalytic capabilities for many hydrocarbon processes. Zeolitic materials typically are ordered porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alkaline-earth-metal cations, ammonium ions, or hydrogen ions.

Prior art developments have resulted in formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590) and others.

Boron is not considered a replacement for aluminum or silicon in a zeolitic composition. However, recently a new crystalline borosilicate molecular sieve AMS-1B with distinctive properties was disclosed in U.S. Pat. Nos. 4,268,420 and 4,269,813 incorporated by reference herein. According to these patents AMS-1B can be synthesized by crystallizing a source of an oxide of silicon, an oxide of boron, an oxide of sodium and an organic template compound such as a tetra-n-propylammonium salt. The process of this invention uses AMS-1B crystalline borosilicate molecular sieve.

Hydrocarbon conversion processes are known using other zeolitic materials. Examples of such processes are dewaxing of oil stock (U.S. Pat. Nos. 3,852,189, 4,211,635 and Re. 28,398); conversion of lower olefins (U.S. Pat. Nos. 3,965,205 and 3,960,978 and European Patent Application No. 31,675); aromatization of olefins and aliphatics (U.S. Pat. Nos. 3,761,389, 3,813,330, 3,827,867, 3,827,868, 3,843,740, 3,843,741 and 3,914,171); hydrocracking and oligomerization of hydrocarbons (U.S. Pat. Nos. 3,753,891, 3,767,568, 3,770,614 and 4,032,432); conversion of ethane to aromatics and $C_3+$ hydrocarbons (U.S. Pat. No. 4,100,218); conversion of straight-chain and slightly branched-chain hydrocarbons to olefins (U.S. Pat. Nos. 4,309,275 and 4,309,276); and conversion of $C_4$ paraffins to aromatics (U.S. Pat. No. 4,291,182).

A method to manufacture isobutylene from a linear alkane such as n-butene would be desirable and a method that would dehydrogenate an alkane and isomerize a carbon structure in one step without excessive losses to undesirable by-products would be especially desirable. Further, a process that converts n-butane to more useful and valuable products such as isobutylene, isobutane, n-butenes and aromatics would be advantageous.

SUMMARY OF THE INVENTION

A process to convert an alkane, such as n-butane, to dehydrogenated and isomerized products comprises contacting such alkane under conversion conditions with an AMS-1B crystalline borosilicate catalyst composition containing an ion or molecule of a catalytically active element, such as noble metal.

BRIEF DESCRIPTION OF THE INVENTION

This invention is a method to convert an alkane, especially a linear alkane, to a mixture of alkenes, branched alkanes and alkenes, and aromatics. More particularly, this invention is a method to convert n-butane to a mixture containing isobutylene, isobutane and n-butene using an AMS-1B crystalline borosilicate-based catalyst system.

Alkanes are saturated hydrocarbons, i.e., molecules containing carbon and hydrogen atoms with the carbon atoms linked through carbon-carbon single bonds.

A normal alkane contains a chain of unbranched carbon atoms and is represented by the formula:

$$H_3C(CH_2)_{n-1}CH_3$$

wherein n is an integer ranging from one to about 20. Other hydrocarbon-based molecules can have a segment containing a linear alkane structure such as represented by:

$$H_3C(CH_2)_nR$$

wherein R is an organic moiety and n is an integer ranging from one to about 20.

An isoalkane contains a methyl group branched at the end of a linear alkane segment as represented by $$\underset{\displaystyle H_3C-CH-(CH_2)_nR}{\overset{\displaystyle CH_3}{|}}$$

ps wherein R is an organic moiety or hydrogen and n is an integer ranging from zero to about 20.

Alkanes which can be converted using the process of this invention include linear alkanes containing up to about 20 carbon atoms such as ethane, propane, n-butane, n-pentane, n-hexane, n-heptane, n-octane, n-nonane, n-decane and n-dodecane. Other suitable alkanes containing up to about 20 carbon atoms include isoalkanes such as isobutane, 2-methylbutane, 2-methylpentane, 2-methylhexane and the like.

For the purposes of this invention a substantially linear alkane includes normal alkanes, hydrocarbon-based molecules containing a linear alkane segment and isoalkanes as described above. Also included, for the purposes of this invention, is isobutane. The preferable substantially linear alkane useful in this invention is n-butane. Mixtures of substantially linear alkanes can be used in the process of this invention.

The substantially linear alkanes, or mixtures thereof, used in the process of this invention can be converted in the presence of other substances such as other hydrocarbon-based molecules. Thus, a feedstream used in the process of this invention comprising a substantially linear alkane also can contain other hydrocarbons such as alkenes, methane, aromatics, hydrogen, and inert gases. A process in which partially reacted hydrocarbons are recycled will contain a mixture including alkanes, alkenes, methane and aromatics. Typically a substantially linear alkane feedstream used in this invention contains about 10 to 100 wt.% substantially linear alkane and preferably contains about 50 to 100 wt.% substantially linear alkane.

The process of this invention can be used in conjunction with other hydrocarbon conversion or refinery processes. For example normal butane obtained from a refinery alkylation unit can be converted to C4 olefins and isobutane.

The catalyst useful in this invention is based on the crystalline borosilicate molecular sieve, AMS-1B, described in U.S. Pat. Nos. 4,268,420 and 4,269,813, incorporated herein by reference. A particularly useful catalyst for this invention contains AMS-1B in which a noble metal is placed by ion exchange, impregnation or other means.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

$$0.9 \pm 0.2 M_{2/n}O:B_2O_3:ySiO_2:zH_2O$$

wherein M is at least one cation, n is the valence of the cation, y is between 4 and about 600 and z is between 0 and about 160.

TABLE I

| d-Spacing Å[1] | Assigned Strength[2] |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

[1] Copper K alpha radiation
[2] VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

| | Broad | Preferred | Most Preferred |
|---|---|---|---|
| SiO$_2$/B$_2$O$_3$ | 5-400 | 10-150 | 10-80 |
| R$_2$O$^+$/[R$_2$O$^+$ + M$_{2/n}$O] | 0.1-1.0 | 0.2-0.97 | 0.3-0.97 |
| OH$^-$/SiO$_2$ | 0.01-11 | 0.1-2 | 0.1-1 |
| H$_2$O/OH$^-$ | 10-4000 | 10-500 | 10-500 | wherein R is an organic compound and M is at least one cation having a valence n, such as an alkali metal or an alkaline earth metal cation. By regulation of the quantity of boron (represented as B$_2$O$_3$) in the reaction mixture, it is possible to vary the SiO$_2$/B$_2$O$_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blendor. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of OH$^-$/SiO$_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about $11.0 \pm 0.2$ using a compatible acid or base such as sodium bisulfate or sodium hydroxide. After sufficient quantities of silicic acid polymer (Ludox) are added with intensive mixing, preferably the pH is again checked and adjusted to a range of about $11.0 \pm 0.2$. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25°–200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Catalyst compositions useful in this invention preferably contain Group VIII elements while most preferably noble metals are used in this invention as catalytically active material. Such noble metals include ruthenium, osmium, rhodium, iridium, palladium and platinum; platinum and palladium are preferable while platinum is the most preferable. Mixtures of noble metals can be used.

In addition, preferable catalyst compositions are prepared containing a noble metal in combination with another metal ion or compound including Groups IB, IIB, IIIB, IVB, VB, VIB, VIIB and VIII metals and rare earth elements. Specific additional catalytic materials include ions and compounds of copper, lanthanum, molybdenum, cobalt, tungsten and nickel. Other additional catalytic materials can be ions and compounds of scandium, yttrium, titanium, zirconium, hafnium, vanadium, niobium, tantalum, chromium, cerium, manganese, iron, zinc and cadmium. Specific combinations of noble metal and other catalytic materials include ions or compounds of platinum and copper, platinum and lanthanum, platinum and cobalt, platinum and nickel, platinum and molybdenum, and platinum and tungsten.

Ion exchange and impregnation techniques are well-known in the art. Typically, an aqueous solution of a cationic species is exchanged one or more times at about 25° to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about thirty weight percent, typically from about 0.05 to about 25 weight percent, depending on the process use intended. The optimum amount can be determined easily by routine experimentation.

The AMS-1B crystalline borosilicate useful in this invention may be used as a pure material in a catalyst or may be admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt.% of the total composition. Catalytic compositions can contain about 0.1 wt.% to about 100 wt.% crystalline borosilicate material and preferably contain about 10 wt.% to about 95 wt.% of such material and most preferably contain about 20 wt.% to about 80 wt.% of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813.

In a process using this invention, a stream of an alkane, such as n-butane, is contacted with a catalytic material-containing AMS-1B borosilicate-based catalyst. Generally, in the preferable process of this invention a linear alkane or molecule containing a linear alkane segment is contacted with the above-described AMS-1B borosilicate-based catalyst system in the liquid or vapor phase at a suitable reaction temperature, pressure and space velocity. Generally, suitable reaction conditions include a temperature of about 250° to about 650° C., a pressure of about 0.1 to about 50 atmospheres (10 to 5,000 kPa) or higher with hydrogen/hydrocarbon molar ratio of 0 to about 10 or higher at a weight hourly space velocity (WHSV) of about 0.1 to about 40 hr$^{-1}$. In a typical process scheme, an n-butane-containing hydrocarbon stream is contacted with such catalyst in a reactor at about 400° to about 600° C. at a pressure of about 0.2 to about 20 atmospheres (20 to 2000 kPa) with a hydrogen/butane molar ratio of 0 to about 10 at a WHSV of about 0.3 to about 25 hr$^{-1}$. Preferably the n-butane conversion process of this invention is conducted at about 450° to about 600° C. at a pressure of about 0.3 to about 2 atmospheres (30 to 200 kPa) with a hydrogen/butane molar ratio of about 0.8 to about 6 at a WHSV of about 0.5 to about 6 hr$^{-1}$.

Although conversion of n-butane is the preferable process of this invention, propane and ethane similarly can be converted to propylene and ethylene although more severe conditions (higher temperature and lower pressures and lower space velocities) typically are used. For conversion of ethane and propane preferable conditions are temperatures at about 500° to about 650° C., space velocities of about 1 to about 25 hu$^{-1}$ and pressures of about 0.1 to about 1 atmosphere.

Figure 1:
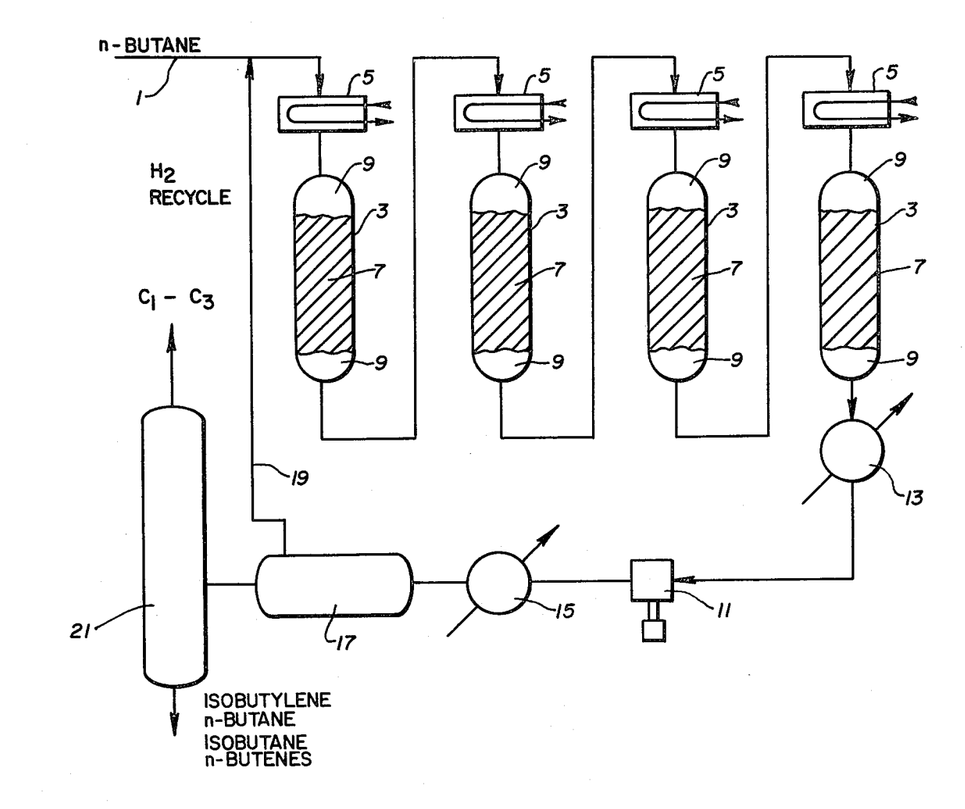
The drawing illustrates a process scheme of this invention in which n-butane is converted to a stream containing butylenes and isobutane.

A typical process scheme is illustrated in the drawing. An n-butane-rich feedstream 1 is passed into a series of reactors 3. The feedstream to each reactor preferably is heated in heaters 5 such that the temperature of catalyst beds 7 in the reactor is maintained at about 400° to about 650° C. Typically, inert material such as alumina balls 9 are placed above and below the catalyst bed in the reactors. A stream of converted material containing isobutylene, n-butene and isobutane is withdrawn from the last reactor in the series after having passed through the catalyst and liquified by compressor 11 and coolers 13 and 15. Hydrogen is separated from the hydrocarbon products in flash drum 17 and can be recycled to the reactors through line 19. Hydrocarbon product containing isobutylene, n-butene, isobutane and n-butane can be transferred to a distillation unit 21 to separate $C_1$-$C_3$ products. Unconverted n-butane may be recycled through the catalyst bed. Typically, the reactors are maintained at about 0.2 to about 20 atmospheres pressure and a hydrogen/butane ratio of 0 to about 10.

The hydrocarbon feed useful in this invention comprises a substantially linear alkane containing two to about 20, preferably three to six carbon atoms. Also considered a linear alkane for purposes of this invention is a compound containing a linear alkane segment with four to about ten carbon atoms. It is believed that long chain linear alkanes and compounds containing linear alkane segments, or a portion of such alkane or segment, may penetrate the molecular sieve structure to contact a catalytic site or contact a catalytic site on the outer surface of the sieve. Thus, the entire molecule need not be small enough to fit entirely within the cavities of the molecular sieve. The preferable feed contains predominantly n-butane although typically minor amounts of other $C_4$ hydrocarbons as well as lighter components may be present. The hydrocarbon feedstream may be diluted with an inert gas such as nitrogen or helium.

The process of this invention converts n-butane to butylenes and isobutane with good selectivity. Typically, 60 to 90 wt.% of the n-butane which is converted forms butylenes and isobutane. It has been demonstrated that increasing temperature or decreasing reactant partial pressure increases selectivity to butylenes while decreasing isobutane.

This invention is demonstrated but not limited by the following Examples.

EXAMPLES I–IX

An AMS-1B borosilicate molecular sieve was prepared according to the teachings of U.S. Pat. No.

4,269,813. A 6.03-gram sample of 20 wt.% AMS-1B crystalline borosilicate molecular sieve containing 0.7 wt.% boron incorporated in a matrix of gamma alumina crushed and sieved to 0.0164–0.0278 inch diameters was added to 6.06 milliliters of water containing 0.0533 grams of $Pt(NH_3)_4Cl_2 \cdot H_2O$. After stirring to obtain uniform wetting of all particles, the molecular sieve containing material was dried for two hours at 165° C. and calcined for 12 hours at 343° C. Analysis determined a platinum content in this material to be 0.54 wt.%.

A 1.56-gram sample of the resultant catalyst material was loaded into a 0.4-inch inside diameter reactor. While purging with hydrogen, the reactor temperature was increased to 523° C. over one hour and held at 523° C. for an additional hour to reduce platinum (II) on the catalyst to platinum metal. A feed on n-butane was contacted in the reactor with the catalyst described above. The conditions and results are summarized in Table II. The data show that n-butane is converted in substantial yield to upgraded products including isobutylene, isobutane and n-butenes.

TABLE II

|  | Examples | | | | | | | | |
|---|---|---|---|---|---|---|---|---|---|
|  | I | II | III | IV | V | VI | VII | VIII | IX |
| Conditions | | | | | | | | | |
| Average Temperature (°C.) | 485 | 513 | 541 | 485 | 512 | 539 | 484 | 512 | 540 |
| Contact Time (sec.) | 0.24 | 0.22 | 0.20 | 0.39 | 0.37 | 0.36 | 0.18 | 0.17 | 0.16 |
| Hydrogen/Hydrocarbon (molar ratio) | 1.6 | 1.6 | 1.6 | 0.78 | 0.78 | 0.78 | 0.78 | 0.78 | 0.78 |
| n-Butane in Feed (mole %)[1] | 100 | 100 | 100 | 100 | 100 | 100 | 28[2] | 28[2] | 28[2] |
| Space Velocity (WHSV, $hr^{-1}$) | 9.0 | 9.0 | 9.0 | 8.2 | 8.2 | 8.2 | 8.2 | 8.2 | 8.2 |
| Product Composition (wt. %) | | | | | | | | | |
| n-Butane | 77.6 | 63.3 | 51.6 | 76.8 | 65.4 | 54.8 | 79.1 | 69.8 | 61.7 |
| Isobutane | 9.44 | 10.1 | 9.09 | 4.31 | 3.95 | 3.46 | 0.72 | 0.79 | 0.95 |
| n-Butenes | 5.04 | 8.41 | 11.8 | 6.16 | 10.1 | 14.3 | 12.0 | 16.5 | 18.6 |
| Isobutylene | 2.57 | 5.12 | 7.61 | 4.10 | 6.73 | 9.32 | 5.99 | 8.63 | 10.9 |
| $C_1$–$C_3$ | 4.24 | 9.84 | 16.4 | 5.70 | 10.5 | 14.2 | 1.75 | 2.81 | 5.93 |
| $C_5+$ | 1.2 | 4.3 | 4.8 | 2.96 | 3.25 | 3.91 | 0.48 | 1.50 | 2.01 |
| Results | | | | | | | | | |
| n-Butane Conversion (wt. %) | 22.4 | 36.7 | 48.4 | 23.2 | 34.6 | 45.2 | 20.9 | 30.2 | 38.3 |
| Selectivity to Total Butylenes (%) | 34.0 | 36.9 | 40.0 | 44.2 | 48.8 | 52.2 | 86.0 | 83.1 | 76.8 |
| Selectivity to Isobutane (%) | 42.1 | 27.5 | 18.8 | 18.6 | 11.4 | 7.65 | 3.41 | 2.60 | 2.48 |
| Selectivity to Isobutane and Butylene (%) | 76.1 | 64.3 | 58.8 | 62.7 | 60.2 | 59.8 | 89.4 | 85.7 | 79.3 |

[1]Based on moles of hydrocarbon
[2]Feed contained 50 mole % helium and 22 mole % hydrogen.

TABLE III

|  | Examples | | |
|---|---|---|---|
|  | X | XI | XII |
| Conditions | | | |
| Average Temperature (°C.) | 481 | 509 | 535 |
| Contact Time (sec.) | 0.30 | 0.29 | 0.28 |
| Hydrogen/Hydrocarbon (molar ratio) | 1.26 | 1.26 | 1.26 |
| Space Velocity (WHSV, $hr^{-1}$) | 8.43 | 8.43 | 8.43 |
| Reactor Pressure (atmos.) | 1.00 | 1.00 | 1.00 |
| Product Composition (wt. %) | | | |
| n-Butane | 91.6 | 86.5 | 83.7 |
| Isobutane | 0.68 | 0.80 | 0.77 |
| n-Butenes | 3.58 | 4.61 | 4.98 |
| Isobutylene | 2.20 | 3.02 | 3.08 |
| $C_1$–$C_3$ | 1.79 | 4.57 | 6.40 |
| $C_5+$ | 0.14 | 2.67 | 1.06 |
| Results | | | |
| n-Butane Conversion (wt. %) | 8.4 | 13.5 | 16.3 |
| Selectivity to Total Butylenes (%) | 68.9 | 56.3 | 49.5 |
| Selectivity to Isobutane (%) | 8.2 | 5.9 | 4.8 |
| Selectivity to Isobutane and Butylene (%) | 77.1 | 62.2 | 54.3 |

EXAMPLES X–XII

Extrudates of 20 wt.% hydrogen form AMS-1B containing 0.4 wt.% boron with 80 wt.% alumina were crushed and sieved to particles having approximate diameters of 0.0164–0.0278 inch as described in Examples I–X. A 4.0 gram portion of such catalyst particles was added to 4.0 grams of water containing 0.0483 grams of dissolved $Pd(NH_3)_4Cl_2 \cdot H_2O$. The mixture was stirred gently and then dried at 165° C. for 16 hours and calcined at 500° C. for four hours. A 0.4-inch inside diameter stainless steel reactor was packed with 1.53 grams of palladium impregnated catalyst with the catalyst secured in place by stainless steel support particles. After reduction of the catalyst with a flowing stream of hydrogen at 523° C., n-butane was passed through the catalyst-packed reactor. Gases exiting the reactor were analyzed by gas chromatography. Results showing conversion of n-butane are shown in Table III.

EXAMPLES XIII–XV

Particles of 20 wt.% AMS-1B on alumina were crushed and sieved as described in Examples X–XII. To a glass dish containing 20.0 grams of such crushed particles were added 20 grams of water containing 0.361 gram of $Pt(NH_3)_4Cl_2 \cdot H_2O$. The mixture was stirred gently and then dried for two hours at 150° C. and calcined at 355° C. for four hours. The 1% platinum impregnated catalyst (1.50 grams) was packed into a reactor as described in Examples X–XII. After reduction in flowing hydrogen at 493° C., 50 milliliters of hydrogen sulfide vapor (23° C., 1 atmosphere) together with hydrogen to form approximately one volume percent concentration were passed over the catalyst. After the hydrogen sulfide/hydrogen flow was discontinued, n-butane flow was started. Results showing n-butane conversion are shown in Table IV.

TABLE IV

|  | Examples | | |
|---|---|---|---|
|  | XIII | XIV | XV |
| Conditions | | | |
| Average Temperature (°C.) | 484 | 511 | 535 |

TABLE IV-continued

|  | Examples | | |
|---|---|---|---|
|  | XIII | XIV | XV |
| Contact Time (sec.) | 0.26 | 0.25 | 0.24 |
| Hydrogen/Hydrocarbon (molar ratio) | 1.7 | 1.7 | 1.7 |
| Space Velocity (WHSV, hr$^{-1}$) | 9.0 | 9.0 | 9.0 |
| Reactor Pressure (atmos.) | 1.07 | 1.07 | 1.07 |
| Product Composition (wt. %) | | | |
| n-Butane | 65.7 | 54.4 | 48.4 |
| Isobutane | 22.2 | 23.5 | 17.6 |
| n-Butenes | 4.11 | 6.75 | 10.6 |
| Isobutylene | 1.80 | 3.87 | 6.36 |
| $C_1$-$C_3$ | 4.84 | 9.41 | 14.2 |
| $C_5$+ | 1.39 | 2.12 | 2.75 |
| Results | | | |
| n-Butane Conversion (wt. %) | 34.0 | 45.6 | 51.6 |
| Selectivity to Total Butylenes (%) | 17.5 | 23.3 | 32.9 |
| Selectivity to Isobutane (%) | 65.6 | 51.5 | 34.2 |
| Selectivity to Isobutane and Butylene (%) | 83.1 | 74.8 | 67.1 |

EXAMPLES XVI-XVIII

Using the catalyst prepared in Examples XIII-XV then n-butane conversion test was operated as described therein except that reaction pressure was reduced to below atmospheric by use of a vacuum pump placed at the reactor outlet. Results of Examples XVI-XVIII are given in Table V and show that reduced reactor pressure increased selectivity to total butylenes and decreased selectivity to isobutane. The amounts of by-products formed also decreased.

TABLE V

|  | Examples | | |
|---|---|---|---|
|  | XVI | XVII | XVIII |
| Conditions | | | |
| Average Temperature (°C.) | 539 | 541 | 541 |
| Contact Time (sec.) | 0.68 | 0.32 | 0.23 |
| Hydrogen/Hydrocarbon (molar ratio) | 1.07 | 1.07 | 1.07 |
| Space Velocity (WHSV, hr$^{-1}$) | 4.1 | 4.1 | 4.1 |
| Reactor Pressure (atmos.) | 1.07 | 0.50 | 0.37 |
| Product Composition (wt. %) | | | |
| n-Butane | 46.6 | 62.1 | 65.1 |
| Isobutane | 11.7 | 2.33 | 1.26 |
| n-Butenes | 9.81 | 15.5 | 16.7 |
| Isobutylene | 6.74 | 10.5 | 10.8 |
| $C_1$-$C_3$ | 22.1 | 7.81 | 5.22 |
| $C_5$+ | 3.08 | 1.79 | 0.86 |
| Results | | | |
| n-Butane Conversion (wt. %) | 53.4 | 27.9 | 34.9 |
| Selectivity to Total Butylenes (%) | 31.0 | 68.5 | 79.0 |
| Selectivity to Isobutane (%) | 21.9 | 6.15 | 3.62 |
| Selectivity to Isobutane and Butylene (%) | 52.9 | 74.7 | 82.6 |

EXAMPLES XIX-XXI

A 4.9-gram sample of hydrogen-form AMS-1B crystalline borosilicate containing 0.44 wt.% boron was mixed with 0.3 gram sterotex binder compressed at 20,000 psig in a one-inch diameter press for five minutes and calcined in air at 500° C. for eight hours to burn off the sterotex binder. To 2.23 grams of crushed and sieved catalyst particles (0.0278-0.0164 inch diameter) were added 2.2 grams of an aqueous solution containing 0.0402 gram of Pt(NH$_3$)$_4$Cl.H$_2$O. The mixture was stirred gently and then dried at 150° C. for four hours and calcined at 355° C. for four hours.

Impregnated catalyst (1.51 grams) was loaded into a reactor, sulfided and tested as described in Examples X-XII. Results are shown in Table VI.

TABLE VI

|  | Examples | | |
|---|---|---|---|
|  | XIX | XX | XXI |
| Conditions | | | |
| Average Temperature (°C.) | 485 | 514 | 542 |
| Contact Time (sec.) | 0.41 | 0.39 | 0.38 |
| Hydrogen/Hydrocarbon (molar ratio) | 1.01 | 1.01 | 1.01 |
| Space Velocity (WHSV, hr$^{-1}$) | 9.02 | 9.02 | 9.02 |
| Reactor Pressure (atmos.) | 1.00 | 1.00 | 1.00 |
| Product Composition (wt. %) | | | |
| n-Butane | 86.7 | 79.1 | 71.6 |
| Isobutane | 3.71 | 3.59 | 2.56 |
| n-Butenes | 5.10 | 8.93 | 12.6 |
| Isobutylene | 3.47 | 6.09 | 8.41 |
| $C_1$-$C_3$ | 0.89 | 1.95 | 4.46 |
| $C_5$+ | 0.14 | 0.32 | 0.40 |
| Results | | | |
| n-Butane Conversion (wt. %) | 13.3 | 20.9 | 28.4 |
| Selectivity to Total Butylenes (%) | 64.4 | 72.0 | 73.9 |
| Selectivity to Isobutane (%) | 27.9 | 17.2 | 9.0 |
| Selectivity to Isobutane and Butylene (%) | 92.3 | 89.1 | 82.9 |

EXAMPLES XXII-XXX

A mixture containing 29.8 grams of alumina sol (9.55 wt.% Al$_2$O$_3$ in water), 14.25 grams of hydrogen-form AMS-1B crystalline borosilicate (0.44 wt.% boron) and 16.0 grams water was blended until free-flowing and homogeneous, after which a solution of 0.309 gram Pt(NH$_3$)$_4$Cl$_2$.H$_2$O in 2.5 grams of water was added followed by additional blending for 10 minutes. The resulting suspension was transferred to a glass dish and 4.1 grams of concentrated ammonium hydroxide was added to gel the mixture and stirred until a pasty-textured mixture was obtained. The resulting semi-solid was dried at 150° C. for four hours and calcined at 300° C. for four hours. The calcined material was crushed and sieved to about 0.0278 to 0.0164 inch particles and 1.88 grams were loaded into a reactor, sulfided and tested as described in Examples X-XII. After reduction in flowing hydrogen at 480° C. the n-butane feed was passed over the catalyst with the results indicating conversion shown in Table VII.

TABLE VII

|  | Examples | | | | | | | | |
|---|---|---|---|---|---|---|---|---|---|
|  | XXII | XXIII | XXIV | XXV | XXVI | XXVII | XXVIII | XXIX | XXX |
| Conditions | | | | | | | | | |
| Average Temperature (°C.) | 475 | 502 | 528 | 478 | 507 | 536 | 505 | 534 | 564 |
| Contact Time (sec.) | 0.47 | 0.46 | 0.44 | 0.57 | 0.55 | 0.53 | 0.7 | 0.7 | 0.6 |
| Hydrogen/Hydrocarbon (molar ratio) | 1.01 | 1.01 | 1.01 | 5.4 | 5.4 | 5.4 | 4.8 | 4.8 | 4.8 |
| Space Velocity (WHSV, hr$^1$) | 13.1 | 13.1 | 13.1 | 3.4 | 3.4 | 3.4 | 1.5 | 1.5 | 1.5 |
| Reactor Pressure (atmos.) | 1.07 | 1.07 | 1.07 | 1.00 | 1.00 | 1.00 | 1.50 | 0.50 | 0.50 |
| Product Composition (wt. %) | | | | | | | | | |
| n-Butane | 82.8 | 75.2 | 69.1 | 85.9 | 75.9 | 64.0 | 70.8 | 60.1 | 50.0 |
| Isobutane | 4.52 | 3.37 | 2.91 | 7.03 | 9.87 | 10.1 | 4.16 | 3.43 | 2.71 |
| n-Butenes | 7.12 | 11.3 | 14.4 | 4.05 | 7.41 | 12.8 | 13.9 | 19.7 | 23.7 |

TABLE VII-continued

|  | Examples | | | | | | | | |
| --- | --- | --- | --- | --- | --- | --- | --- | --- | --- |
|  | XXII | XXIII | XXIV | XXV | XXVI | XXVII | XXVIII | XXIX | XXX |
| Isobutylene | 3.78 | 6.69 | 8.91 | 1.67 | 4.31 | 8.20 | 9.22 | 13.1 | 15.3 |
| $C_1$-$C_3$ | 1.275 | 2.51 | 3.60 | 1.24 | 2.52 | 4.83 | 1.95 | 3.56 | 7.04 |
| $C_5+$ | 0.51 | 0.87 | 1.09 | 0.16 | 0 | 0.13 | 0 | 0 | 1.23 |
| Results |  |  |  |  |  |  |  |  |  |
| n-Butane Conversion (wt. %) | 17.2 | 24.8 | 30.9 | 14.1 | 24.1 | 36.0 | 29.2 | 39.9 | 50.0 |
| Selectivity to Total Butylenes (%) | 63.4 | 72.8 | 75.4 | 40.4 | 48.6 | 58.2 | 79.1 | 82.5 | 78.1 |
| Selectivity to Isobutane (%) | 26.3 | 13.6 | 9.41 | 49.7 | 40.9 | 28.0 | 14.2 | 8.62 | 5.42 |
| Selectivity to Isobutane and Butylene (%) | 89.7 | 86.4 | 84.8 | 90.1 | 89.5 | 86.2 | 93.3 | 91.1 | 83.5 |

EXAMPLES XXXI–XXXIII

Catalyst was prepared and tested as described in Examples XXII–XXX except only 0.031 gram of Pt(NH$_3$)$_4$Cl$_2$.H$_2$O was used to form a material containing 0.1 wt.% platinum. Results are shown in Table VIII.

EXAMPLES XXXIV–XXXVII

Catalyst (1.88 grams) prepared in Examples XXII–XXX was reduced in flowing hydrogen at 550° C. and mixtures of ethane and hydrogen were passed over the reduced catalyst in the previously-described reactor. Results are shown in Table IX demonstrating conversion of ethane.

EXAMPLES XXXVIII–XLV

The process of Examples XXXIV–XXXVII was repeated except a feed mixture of propane and hydrogen was used. Results are shown in Table X.

TABLE VIII

|  | Examples | | |
| --- | --- | --- | --- |
|  | XXXI | XXXII | XXXIII |
| Conditions |  |  |  |
| Average Temperature (°C.) | 473 | 540 | 564 |
| Contact Time (sec.) | 0.65 | 0.60 | 0.59 |
| Hydrogen/Hydrocarbon (molar ratio) | 4.5 | 4.5 | 4.5 |
| Space Velocity (WHSV, hr$^{-1}$) | 3.9 | 3.9 | 3.9 |
| Reactor Pressure (atmos.) | 1.12 | 1.12 | 1.14 |
| Product Composition (wt. %) |  |  |  |
| n-Butane | 88.5 | 72.4 | 70.6 |
| Isobutane | 3.25 | 3.16 | 2.37 |
| n-Butenes | 4.69 | 12.1 | 12.9 |
| Isobutylene | 2.95 | 8.22 | 8.73 |
| $C_1$-$C_3$ | 0.67 | 4.16 | 5.08 |
| $C_5+$ | 0.09 | 0 | 0 |
| Results |  |  |  |
| n-Butane Conversion (wt. %) | 11.6 | 27.6 | 29.4 |
| Selectivity to Total Butylenes (%) | 66.1 | 73.5 | 73.4 |
| Selectivity to Isobutane (%) | 28.1 | 11.4 | 8.0 |
| Selectivity to Isobutane and Butylene (%) | 94.2 | 84.9 | 81.4 |

TABLE IX

|  | Examples | | | |
| --- | --- | --- | --- | --- |
|  | XXXIV | XXXV | XXXVI | XXXVII |
| Conditions |  |  |  |  |
| Average Temperature (°C.) | 569 | 569 | 568 | 565 |
| Contact Time (sec.) | 0.95 | 0.43 | 0.22 | 0.61 |
| Hydrogen/Hydrocarbon (molar ratio) | 1.8 | 1.8 | 1.8 | 0[(1)] |
| Space Velocity (WHSV, hr$^{-1}$) | 2.4 | 2.4 | 2.4 | 2.4 |
| Reactor Pressure (atmos.) | 1.10 | 0.50 | 0.25 | 0.25 |
| Product Composition (wt. %) |  |  |  |  |
| Ethane | 87.1 | 85.4 | 82.4 | 72.9 |
| Ethylene | 4.67 | 6.58 | 11.6 | 24.2 |
| Methane | 7.78 | 7.17 | 5.5 | 1.19 |
| $C_3+$ | 0.45 | 0.85 | 0.47 | 1.71 |
| Ethane Conversion (%) | 12.9 | 14.6 | 17.6 | 27.1 |
| Selectivity to Ethylene | 36.2 | 45.1 | 65.9 | 89.3 |

[(1)]$C_2H_6$ only

TABLE X

|  | Examples | | | | | | | |
| --- | --- | --- | --- | --- | --- | --- | --- | --- |
|  | XXXVIII | XXXIX | XL | XLI | XLII | XLIII | XLIV | XLV |
| Conditions |  |  |  |  |  |  |  |  |
| Average Temperature (°C.) | 510 | 538 | 567 | 509 | 538 | 566 | 556 | 561 |
| Contact Time (sec.) | 0.48 | 0.46 | 0.45 | 0.45 | 0.43 | 0.41 | 0.42 | 0.40 |
| Hydrogen/Hydrocarbon (molar ratio) | 1.9 | 1.9 | 1.9 | 1.9 | 1.9 | 1.9 | 0[(1)] | 0[(1)] |
| Space Velocity (WHSV, hr$^{-1}$) | 6.9 | 6.9 | 6.9 | 3.5 | 3.5 | 3.5 | 10.2 | 5.3 |
| Reactor Pressure (atmos.) | 1.07 | 1.07 | 1.07 | 0.50 | 0.50 | 0.50 | 0.50 | 0.25 |
| Product Composition (wt. %) |  |  |  |  |  |  |  |  |
| Propane | 88.7 | 79.8 | 66.7 | 81.1 | 67.8 | 52.9 | 60.0 | 60.4 |
| Propylene | 5.88 | 10.3 | 16.3 | 11.4 | 18.5 | 26.7 | 35.7 | 36.2 |
| $C_1$-$C_2$ | 4.99 | 9.25 | 15.4 | 6.99 | 12.7 | 18.3 | 2.49 | 2.05 |
| $C_4+$ | 0.37 | 0.68 | 1.43 | 0.43 | 1.01 | 2.10 | 1.68 | 1.32 |
| Propane Conversion (%) | 11.2 | 20.3 | 33.2 | 18.9 | 32.2 | 47.1 | 40.0 | 39.6 |
| Selectivity to Propylene | 52.3 | 50.8 | 49.0 | 60.6 | 57.6 | 56.7 | 89.4 | 91.3 |

[(1)]$C_3H_8$ only

EXAMPLES XLVI–LIV

A series of molecular sieve-based catalyst compositions were prepared in which various metals were incorporated. Lanthanum, nickel and cobalt-exchanged products were prepared by exchanging 30 grams of powdered AMS-1B crystalline borosilicate molecular sieve in the hydrogen form (H-AMS-1B) in 1.0 liter of 0.2 molar solution of metal nitrate with stirring overnight. This procedure was repeated twice except for the nickel-exchanged product. A final exchange solution was performed in 0.4 molar nitrate at a pH of 7 adjusted by dropwise addition of 28% aqueous ammonia. After the final exchange, the sieves were water-washed three times, mixed with sufficient water to form a slurry and added to 1200 grams of PHF alumina sol (10.3 wt.% solids) in a blender. After blending, aqueous ammonia was added to gel the sol.

A copper-exchanged molecular sieve was prepared similarly by exchanging 30.0 grams of H-AMS-1B once with one liter of 0.1 M aqueous cupric acetate solution and twice with one liter of 0.2 M aqueous cupric acetate. After the final exchange, the sieve was mixed with sufficient water to form a slurry and added to 1200 grams of PHF alumina sol (10.3 wt.% solids) and blended. Aqueous ammonia then was added to form a gel.

Tungsten and molybdenum catalysts were prepared similarly except metal carbonyl was used as the starting material. For example, 4.59 grams of molybdenum dissolved in benzene were added to 28.5 grams of sieve and the resulting solution evaporated to dryness and the product calcined. In a similar preparation, 1.91 grams of tungsten hexacarbonyl were dissolved in chloroform and the mixture added to 20.0 grams of sieve, dried and calcined. The molybdenum- and tungsten-treated sieves were mixed with alumina sol and gelled.

In all cases, gels were dried at 121° C., ground to 12-28 mesh and calcined at 538° C. in air for 24 hours. Sieves in a gamma alumina containing 0.6 wt.% platinum were prepared by dissolving $(NH_4)_2PtCl_4$ in water (0.0308 M) and impregnating to a point of incipient wetness. The resulting sieves were air-dried for one hour, dried at 121° C. and calcined at 538° C. in air for 24 hours.

Catalyst performance was evaluated in a fixed-bed, downflow, 18-inch by one-half inch inside diameter, Vycor reactor in which 10.0 grams of catalyst were held in place by a glass wool plug set on three dimples located twelve inches from the top of the tube. Hydrogen and hydrocarbon feed were metered individually to the reactor. Reactor effluent was analyzed through a sample loop by gas chromatography. In a typical run, hydrogen flow was started and heat turned on. Twenty minutes after reaction temperature was reached, hydrocarbon was introduced and twelve minutes later the gas chromatograph sample loop was charged and injected.

Comparative Runs A, B and C were performed using 20 wt.% platinum-exchanged, hydrogen-form ZSM-5 crystalline aluminosilicate in a gamma alumina matrix.

Results are shown in Table XI. The data show that AMS-1B crystalline borosilicate molecular sieve catalyst containing platinum converts butane to other hydrocarbon products including isobutylene, isobutane, butenes and aromatics with relatively low $C_1$-$C_2$ and coke production.

TABLE XI

| Catalyst Composition | Ex. XLVI Pt, H—AMS—1B | Ex. XLVII Pt, H—AMS—1B | Ex. XLVIII Pt, Cu—AMS—1B | Ex. XLIX Pt, Mo—AMS—1B | Ex. L Pt, La—AMS—1B | Ex. LI Pt, Co—AMS—1B |
|---|---|---|---|---|---|---|
| Temperature (°C.) | 454 | 510 | 454 | 454 | 454 | 454 |
| Product Composition (wt. %) | | | | | | |
| Nonaromatic | | | | | | |
| $C_1$ | 7.4 | 6.6 | 2.1 | 8.9 | 11.1 | 11.8 |
| $C_2$ | 6.6 | 6.7 | 4.7 | 8.4 | 9.7 | 10.5 |
| $C_3$ | 12.0 | 12.5 | 11.8 | 12.9 | 14.7 | 15.0 |
| Isobutane | 12.6 | 7.3 | 19.5 | 15.2 | 14.1 | 14.8 |
| Isobutylene, 1-butene | 5.6 | 7.7 | 6.5 | 4.7 | 4.3 | 3.5 |
| n-butane | 18.9 | 12.8 | 29.8 | 24.1 | 22.1 | 22.6 |
| trans-2-butene | (1) | 4.4 | (1) | (1) | (1) | (1) |
| cis-2-butene | 3.4 | 4.4 | 4.0 | 2.6 | 2.2 | 1.9 |
| $C_5$ | 13.7 | 7.4 | 9.2 | 7.8 | 6.8 | 5.1 |
| $C_6$ | 1.0 | 0.7 | 0.6 | 0.7 | 0.5 | 0.4 |
| $C_7$ | 0 | 0.2 | 0 | 0 | 0 | 0 |
| Aromatics | | | | | | |
| $C_6$ | 5.0 | 5.9 | 1.7 | 2.8 | 3.0 | 2.8 |
| $C_7$ | 5.1 | 8.3 | 1.7 | 3.4 | 4.1 | 4.1 |
| $C_8$ | 6.8 | 11.0 | 7.4 | 6.8 | 5.9 | 5.9 |
| $C_9+$ | 1.4 | 2.8 | 0.7 | 0.9 | 0.7 | 0.6 |
| Feed Lost as Coke (mole %) | 0.3 | 0.7 | 0.3 | 0.8 | 0.9 | 1.1 |

| Catalyst Composition | Ex. LII Pt, W—AMS—1B | Ex. LIII Pt, Ni—AMS—1B | Ex. LIV Pt, Ni—AMS—1B | Run A Pt—H—ZSM—5 | Run B Pt—H—ZSM—5 | Run C Pt—H—ZSM—5 |
|---|---|---|---|---|---|---|
| Temperature (°C.) | 454 | 454 | 510 | 399 | 454 | 510 |
| Product Composition (wt. %) | | | | | | |
| Nonaromatic | | | | | | |
| $C_1$ | 10.4 | 13.8 | 15.3 | 6.1 | 9.3 | 10.6 |
| $C_2$ | 9.1 | 7.2 | 9.4 | 6.8 | 11.3 | 13.8 |
| $C_3$ | 13.8 | 7.9 | 3.9 | 14.7 | 21.3 | 13.8 |
| Isobutane | 14.8 | 10.0 | 4.8 | 18.2 | 11.2 | 7.3 |
| Isobutylene, 1-butene | 6.0 | 5.2 | 5.5 | 0.8 | 1.5 | 2.2 |
| n-butane | 25.9 | 14.7 | 10.6 | 26.9 | 13.5 | 9.8 |
| trans-2-butene | (1) | 2.7 | 2.6 | (1) | (1) | (1) |
| cis-2-butene | 3.5 | 2.2 | 2.0 | 0.7 | 0.5 | 1.1 |
| $C_5$ | 5.2 | 4.4 | 0.6 | 17.9 | 4.3 | 1.3 |
| $C_6$ | 0.5 | 0.3 | 0 | 1.2 | 0.1 | 0.1 |
| $C_7$ | 0 | 0 | 0 | 0 | 0 | 0 |
| Aromatics | | | | | | |

TABLE XI-continued

| | | | | | | |
|---|---|---|---|---|---|---|
| $C_6$ | 1.9 | 7.4 | 11.8 | 2.4 | 7.8 | 8.6 |
| $C_7$ | 2.8 | 7.1 | 9.9 | 1.8 | 10.7 | 12.6 |
| $C_8$ | 5.3 | 5.5 | 6.5 | 1.8 | 6.5 | 9.6 |
| $C_9+$ | 0.4 | 5.5 | 0.5 | 0 | 0.9 | 1.5 |
| Feed Lost as Coke (mole %) | 0.5 | 5.2 | 16.6 | 0.7 | 1.0 | 0.5 |

[1] Included in cis-2-butene

What is claimed is:

1. A process to convert a substantially linear alkane to dehydrogenated and isomerized products comprising contacting such alkane under conversion conditions comprising a temperature of about 250° to about 650° C., a pressure of about 0.1 to about 50 atmospheres, a hydrogen/hydrocarbon molar ratio of 0 to about 10 and a weight hourly space velocity of about 0.1 to about 40 $hr^{-1}$ with an AMS-1B crystalline borosilicate-based catalyst composition containing an ion or molecule of a noble metal.

2. The process of claim 1 wherein the substantially linear alkane comprises a normal alkane having two to twenty carbon atoms or an organic compound containing a linear alkane segment having three to twenty carbon atoms.

3. The process of claim 2 wherein the alkane is a normal alkane having two to twenty carbon atoms or an isoalkane containing a linear alkane segment having three to twenty carbon atoms.

4. The process of claim 1 wherein the alkane is a normal alkane having two to about twenty carbon atoms.

5. The process of claim 4 wherein the linear alkane is ethane, n-propane, n-butane, n-pentane or n-hexane.

6. The process of claim 5 wherein the linear alkane is n-butane.

7. The process of claim 5 wherein the substantially linear alkane comprises from about 10 to 100 wt.% of a feedstream contacting the catalyst.

8. The process of claim 1 wherein the noble metal is platinum or palladium.

9. The process of claim 8 wherein the noble metal is platinum.

10. The process of claim 8 wherein an ion or molecule of a Group IB, IIIB, IVB, VB, VIB, VIIB or VIII metal or a rare earth element is contained in the AMS-1B borosilicate-based composition as an additional catalytically active material.

11. The process of claim 10 wherein the additional catalytically active material is copper, lanthanum, molybdenum, cobalt, tungsten, nickel or zinc.

12. The process of claims 8, 9, 10 or 11 wherein the alkane is ethane, n-propane or n-butane, n-pentane or n-hexane.

13. The process of claims 8, 9, 10 or 11 wherein the alkane is n-butane.

14. The process of claim 1 wherein the AMS-1B crystalline borosilicate composition is incorporated within an alumina, silica, magnesia or silica-alumina matrix.

15. The process of claim 14 wherein the AMS-1B crystalline borosilicate content in the matrix ranges from about 10 to about 95 wt.%.

16. The process of claim 15 wherein the AMS-1B crystalline borosilicate content in the matrix ranges from about 20 to about 80 wt.%.

17. The process of claim 1 wherein the conversion conditions are a temperature of about 400° to about 600° C., a pressure of about 0.2 to about 20 atmospheres, a hydrogen/hydrocarbon molar ratio of 0 to about 10 and a weight hourly space velocity of about 0.3 to about 25 $hr^{-1}$.

18. The process of claim 1 wherein the alkane is an isoalkane.

19. The process of claim 18 wherein the isoalkane is isobutane, 2-methylbutane, 2-methylpentane, 2-methylhexane.

20. A process to convert n-butane to a mixture comprising dehydrogenated and isomerized products comprising contacting n-butane under conversion conditions comprising a temperature of about 400° to about 600° C., a pressure of about 0.2 to about 20 atmospheres, a hydrogen/butane molar ratio of 0 to about 10 and a weight hourly space velocity of about 0.3 to about 25 $hr^{-1}$ with a catalyst composition comprising AMS-1B crystalline borosilicate containing an ion or molecule of a noble metal.

21. The process of claim 20 wherein n-butane is converted at about 500° to about 600° C. at a pressure of about 0.3 to about 2 atmospheres with a hydrogen/butane molar ratio of about 0.8 to about 6 and a weight hourly space velocity of about 0.5 to about 6 $hr^{-1}$.

22. The process of claims 20, or 21 wherein the noble metal is platinum or palladium.

23. The process of claims 20, or 21 wherein an ion or molecule of a Group IB, IIB, IIIB, IVB, VB, VIB, VIIB or VIII metal or a rare earth element is contained in the catalyst composition.

24. The process of claims 20, or 21 wherein an ion or molecule of copper, lanthanum, molybdenum, cobalt, tungsten, nickel or zinc is contained in the catalyst composition.

25. The process of claim 20 wherein unconverted n-butane is recycled over the catalyst composition.

26. The process of claim 20 wherein n-butane is converted to a mixture comprising isobutylene, isobutane and butenes.

27. The process of claims 20, or 21 wherein n-butane comprises about 10 to 100 wt.% of a feedstream contacting the catalyst.

28. The process of claims 20, or 21 wherein n-butane comprises about 50 to 100 wt.% of a feedstream contacting the catalyst.

* * * * *

UNITED STATES PATENT OFFICE
CERTIFICATE OF CORRECTION

Patent No. 4,433,190          Dated February 21, 1984

Inventor(s) David L. Sikkenga, Thomas D. Nevitt and Norman F. Jerome

It is certified that error appears in the above-identified patent and that said Letters Patent are hereby corrected as shown below:

| Col. | Line | |
|---|---|---|
| 3 | 23 | "ps" and should read -- -- (delete) |
| 8 | 17 | "hu$^{-1}$" and should read --hr$^{-1}$-- |
| 9 | 17 | "on" and should read --of-- |
| 11 | 23 | "then" and should read --the-- |
| 17 | 41 | "5" and should read --1-- |
| 17 | 48 | "Group IB, IIIB," and should read --Group IB, IIB, IIIB,-- |

Signed and Sealed this

Thirtieth Day of July 1985

[SEAL]

Attest:

DONALD J. QUIGG

Attesting Officer      Acting Commissioner of Patents and Trademarks